United States Patent [19]

Grosskinsky et al.

[11] Patent Number: 4,576,804

[45] Date of Patent: Mar. 18, 1986

[54] STABILIZED SOLUTIONS OF HYDROXYLAMINE OR ITS SALTS

[75] Inventors: Otto-Alfred Grosskinsky; Elmar Frommer; Josef Ritz, all of Ludwigshafen; Erwin Thomas, Freinsheim; Franz-Josef Weiss, Neuhofen, all of Fed. Rep. of Germany

[73] Assignee: BASF Aktiengesellschaft, Fed. Rep. of Germany

[21] Appl. No.: 677,306

[22] Filed: Dec. 3, 1984

[30] Foreign Application Priority Data

Dec. 2, 1983 [DE] Fed. Rep. of Germany ....... 3343600

[51] Int. Cl.⁴ .............................................. C01B 21/14
[52] U.S. Cl. .................................... 423/265; 423/387
[58] Field of Search ...................... 423/387, 388, 265

[56] References Cited

U.S. PATENT DOCUMENTS 2,145,082  8/1964  Rausch .
3,480,391 11/1969  Carlos .
3,480,392 11/1969  Carlos .
3,544,270 12/1970  Carlos .

FOREIGN PATENT DOCUMENTS 100908  6/1982  Japan ................................... 423/387
 69842  4/1983  Japan ................................... 423/387
 69844  4/1983  Japan ................................... 423/387
 69843  4/1983  Japan ................................... 423/387
 69841  4/1983  Japan ................................... 423/387
7703020  9/1978  Netherlands ....................... 423/387

*Primary Examiner*—John Doll
*Assistant Examiner*—Wayne A. Langel
*Attorney, Agent, or Firm*—Keil & Weinkauf

[57] ABSTRACT

Stabilized solutions of hydroxylamine or its salts in water or alcohols, containing hydroxyanthraquinones, and their preparation.

6 Claims, No Drawings

STABILIZED SOLUTIONS OF HYDROXYLAMINE OR ITS SALTS

Solutions of hydroxylammonium salts decompose slowly at room temperature and more rapidly at elevated temperatures, this behavior being more pronounced in the case of solutions of free hydroxylamine. There has been no lack of attempts to stabilize solutions of hydroxylamine and its salts in order to achieve a longer shelf life. For example, according to U.S. Pat. No. 3,544,270, urea derivatives are used as stabilizers, and U.S. Pat. No. 3,480,391 recommends amidoximes as suitable stabilizers. According to U.S. Pat. No. 3,480,392, hydroxamic acids, too, can be used for stabilizing hydroxylamine. Furthermore, U.S. Pat. No. 3,145,082 discloses the use of chelate-forming agents, such as sodium ethylenediaminetetraacetate, as stabilizers. The stabilizers used to date are unsatisfactory.

It is an object of the present invention to provide stabilized solutions of hydroxylamine or its salts which are stable over a prolonged period and in which, in particular, the decomposition of free hydroxylamine is minimized.

We have found that this object is achieved by stabilized solutions of hydroxylamine or its salts in water or alcohols, which contain hydroxyanthraquinones.

The present invention furthermore relates to a process for the preparation of stabilized solutions of hydroxylamine or its salts by the addition of stabilizers, wherein the molecular oxygen dissolved in the solution to be stabilized is removed from this solution by treatment with nitrogen which is free of molecular oxygen, and hydroxyanthraquinones are then added.

The solutions of hydroxylamine or its salts which have been stabilized according to the invention have the advantage that they are stable over a longer period than prior art solutions, and in particular the decomposition of free hydroxylamine is reduced to a minimum.

According to the invention, a solution of hydroxylamine or one of its salts in water or an alcohol, eg. a $C_1$–$C_4$-alkanol, is used as the starting material. Examples of suitable salts of hydroxylamine are those with a strong mineral acid, such as sulfuric acid, nitric acid or hydrochloric acid, or those with fatty acids, eg. acetic acid or propionic acid. Because of the difference in solubilities, hydroxylamine is preferably in the form of a solution in water or an alcohol, whereas its salts are preferably present as aqueous solutions. The contents of hydroxylamine or its salts is, as a rule, from 10 to 70% by weight, and such solutions generally have a pH of from 8 to 11. Particularly preferably, aqueous solutions are used as starting materials.

The stabilizers used are hydroxyanthraquinones, in particular those which contain two or more hydroxyl groups. Preferred hydroxyanthraquinones are those of the formula

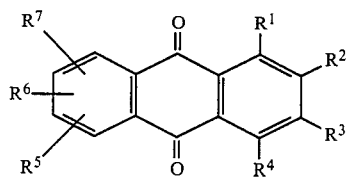

I where $R^1$, $R^2$, $R^3$, $R^4$, $R^5$, $R^6$ and $R^7$ are each hydrogen, hydroxyl or $C_1$–$C_4$-alkoxy and $R^3$ may furthermore be methyl, with the proviso that two or more substituents are hydroxyl. In particularly preferred hydroxyanthraquinones of the formula I, $R^1$, $R^2$, $R^3$, $R^4$, $R^5$, $R^6$ and $R^7$ are each hydrogen, hydroxyl or methoxy, with the proviso that 2 or more substituents are hydroxyl. The hydroxyl-containing hydroxyanthraquinones can also be present in the form of glycosides. Examples of suitable hydroxyanthraquinones are 1,2-dihydroxyanthraquinone, 1,4-dihydroxyanthraquinone, 1,2,4-trihydroxyanthraquinone, 2,3-dihydroxyanthraquinone, 1,5-dihydroxyanthraquinone, 1,8-dihydroxyanthraquinone, 1,2,6-trihydroxyanthraquinone, 1,2,7-trihydroxyanthraquinone, 1,2,5,8-tetrahydroxyanthraquinone, 1,2,4,5,8-pentahydroxyanthraquinone, 1,6,8-trihydroxy-3-methylanthraquinone, 1,8-dihydroxy-3-methylanthraquinone and 1,8-dihydroxy-3-methyl-6-methoxyanthraquinone. Advantageously, hydroxyanthraquinones are used in amounts of from 0.005 to 1, in particular from 0.01 to 0.1, % by weight, based on the solution to be stabilized. The presence of polyhydroxybenzenes, in particular pyrogallol, in addition has also proven useful, the polyhydroxybenzenes advantageously being added in amounts of from 0.005 to 0.1% by weight, based on the solution to be stabilized. It is noteworthy that the combined use of hydroxyanthraquinones and polyhydroxybenzenes results in a synergistic effect.

Stabilized solutions of hydroxylamine or its salts in water or in alcohols are prepared, according to the invention, by a method in which the molecular oxygen dissolved in the solution to be stabilized is first displaced from this solution by treatment with nitrogen which is free of molecular oxygen. This is achieved by, for example, passing oxygen-free nitrogen through the solution to be stabilized, for example for from 5 to 10 minutes. The nitrogen used for this purpose advantageously contains less than 2 ppm of oxygen. Hydroxyanthraquinones and, if required, polyhydroxybenzenes are then added, and are dissolved in the said solution. It is also possible to add the stabilizers in the form of solutions, eg. in a $C_1$–$C_4$-alkanol, to the solution to be stabilized. The temperature is advantageously maintained at 5°–40° C. during this procedure.

It is of course advantageous if the solution to be stabilized is prevented from becoming contaminated with heavy metals, in particular copper or noble metals, since these catalyze the decomposition of hydroxylamine. It is also advantageous to exclude high-energy radiation by means of suitably colored glass containers, and to store the stabilized solutions at below 40° C., for example at from 5° to 20° C.

Stabilized solutions of hydroxylamine or its salts are useful for the preparation of oximes.

The Example which follows illustrates the subject of the invention.

EXAMPLE

An aqueous solution of hydroxylamine is gassed with oxygen-free nitrogen at 20° C. for 10 minutes. The concentration of hydroxylamine, the type and amount of stabilizer and the results achieved as a function of time and temperature are shown in the Table below.

TABLE

| Stabilizer | °C. | | | | | |
|---|---|---|---|---|---|---|
| 50 ppm Quinalizarine | 5 | 0 | 480 | 622 | 1506 | Hours |
| | | 141,37 | 141,32 | 141,22 | 140,61 | g/l NH$_2$OH |
| 50 ppm Quinalizarine | 20 | 0 | 480 | 619 | 1504 | Hours |
| | | 141,21 | 139,92 | 139,76 | 137,97 | g/l |

TABLE-continued

| Stabilizer | °C. | | | | | |
|---|---|---|---|---|---|---|
| 50 ppm Quinalizarine | 40 | 0 141,05 | 480 139,20 | 618 138,60 | 1486 135,99 | Hours NH$_2$OH g/l NH$_2$OH |

We claim:

1. A stabilized solution of hydroxylamine or its salts in water or an alcohol, which contains a hydroxyanthraquinone.

2. A stabilized solution as claimed in claim 1, which contains a hydroxyanthraquinone of the formula

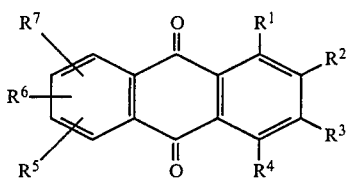

I where $R^1$, $R^2$, $R^3$, $R^4$, $R^5$, $R^6$ and $R^7$ are each hydrogen, hydroxyl or $C_1$–$C_4$-alkoxy and $R^3$ may furthermore be methyl, with the proviso that two or more substituents are hydroxyl.

3. A stabilized solution as claimed in claim 1, which contains a hydroxyanthraquinone of the formula

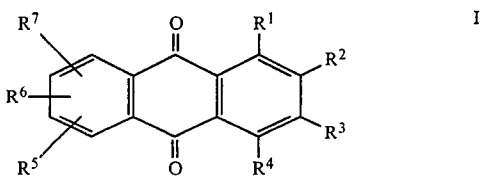

I where $R^1$, $R^2$, $R^3$, $R^4$, $R^5$, $R^6$ and $R^7$ are each hydrogen, hydroxyl or methoxy and $R^3$ may furthermore be methyl, with the proviso that two or more substituents are hydroxyl.

4. A stabilized solution as claimed in claim 1, which contains from 0.005 to 1% by weight, based on the solution to be stabilized, of a hydroxyanthraquinone.

5. A stabilized solution as claimed in claim 1, which additionally contains pyrogallol.

6. A process for the preparation of a stabilized solution of hydroxylamine or its salts in water or an alcohol, wherein the molecular oxygen dissolved in the solution to be stabilized is removed from this solution by treatment with nitrogen which is free of molecular oxygen, and a hydroxyanthraquinone is then added.

* * * * *